United States Patent
Araki et al.

[11] Patent Number: 5,914,070
[45] Date of Patent: Jun. 22, 1999

[54] GAS CONCENTRATION ADJUSTING AGENT, GAS CONCENTRATION ADJUSTING METHOD, AND GAS CONCENTRATION ADJUSTING SYSTEM

[75] Inventors: Hisaya Araki, Tokyo; A-Hon Kwon; Tomoo Kamiya, both of Osaka; Yoshihiko Harima, Tokyo, all of Japan

[73] Assignee: Mitsubishi Gas Chemical Company, Inc., Tokyo, Japan

[21] Appl. No.: 08/823,543

[22] Filed: Mar. 25, 1997

[30] Foreign Application Priority Data

Mar. 26, 1996 [JP] Japan .................................. 8-070033

[51] Int. Cl.⁶ .......................... C09K 15/02; C09K 15/06; C09K 15/34; C12M 3/00
[52] U.S. Cl. .................. 252/188.28; 435/284.1; 435/404; 435/809; 435/801; 435/325
[58] Field of Search ................. 252/188.28; 435/240.2, 435/240.3, 240.4, 240.54, 809, 801, 41, 325, 373, 404, 284.1

[56] References Cited

U.S. PATENT DOCUMENTS

| | | | |
|---|---|---|---|
| 4,384,972 | 5/1983 | Nakamura et al. ................. | 252/188.21 |
| 5,180,518 | 1/1993 | Sugihara et al. ................... | 252/188.28 |
| 5,458,875 | 10/1995 | Casas-Perez et al. ............... | 424/93.45 |
| 5,476,780 | 12/1995 | Watanabe ............................. | 435/240.2 |

*Primary Examiner*—Joseph D. Anthony
*Attorney, Agent, or Firm*—Sixbey Friedman Leedom & Ferguson; Thomas W. Cole

[57] ABSTRACT

A gas concentration adjusting agent which allows a low oxygen concentration environment, such as an ischemic environment for tests of cultured cell damage caused by low oxygen or the like, to be conveniently created, as well as a method and a system for adjusting gas concentrations using this easily handled agent, are provided. During the culture of cultured cells under low oxygen-ischemic culture conditions in a sealed container, the gas concentration adjusting agent consisting of water, a carbon dioxide absorbent, and an ascorbic acid-based, carbon dioxide-generating type of oxygen-absorbing composition is sealed inside the sealed container, so as to adjust the oxygen concentration in the culture environment to no more than 1% and the carbon dioxide concentration to between 3 and 7%.

7 Claims, 4 Drawing Sheets

● : low oxygen injury test (2 hours) group
○ : control (no low oxygen time)
▲ : low oxygen injury test (3 hours) group
△ : control (no low oxygen time)
■ : low oxygen injury test (4 hours) group
□ : control (no low oxygen time)

GAS CONCENTRATION ADJUSTING AGENT, GAS CONCENTRATION ADJUSTING METHOD, AND GAS CONCENTRATION ADJUSTING SYSTEM

BACKGROUND OF THE INVENTION

1. Field of the Invention

The present invention relates to a gas concentration adjusting agent, gas concentration adjusting method, and gas concentration adjusting system, and in particular to a gas concentration adjusting agent that conveniently brings about a low oxygen concentration environment with an oxygen concentration of no more than 1% and a carbon dioxide concentration of between 3 and 7%, for example, an ischemic environment which is necessary for basic research intended to study damage in various organs and viscera at the molecular level during ischemic conditions which prevail in the absence of sufficient circulation of blood to organs and viscera in the course of surgery, cardiac arrest, and organ transplants, as well as to a method and a system for adjusting gas concentrations using this agent.

2. Description of Related Art

A conventional method primarily used to create a low oxygen concentration environment to test cultured cells in ischemic environments has been to connect a vacuum pump and a cylinder filled with a mixed gas consisting of nitrogen and carbon dioxide having a regulated carbon dioxide concentration to a pressure-tight sealed container serving as the culture container, and to repeatedly suction off the gas inside the aforementioned sealed container and supply the mixed gas, so as to place the interior of the container under carbon dioxide-containing nitrogen.

However, this method for forcible gas displacement using the aforementioned pressure-tight sealed container suffers from drawbacks such as the need for large-scale equipment, troublesome and complicated handling, and the need for equipment maintenance. Particularly in the case of tests which undergo changes in the state of the cultured cells over time, gas displacement is required for several containers. Problems that result are the time-consuming nature of the enterprise and the difficulty in establishing uniform test conditions.

Methods involving the use of agents for adjusting the culture environment have also been employed, and anaerobic culture agents which are used to culture anaerobic bacteria, such as "Gaspack" (by BBL) and "Anaeropack" (by Mitsubishi Gas Chemical Company Inc.), have been used as such agents for adjusting culture environments.

However, methods involving the use of these agents for adjusting culture environments have also been plagued with problems such as those given below.

When "Gaspack" is used, for example, water must be added, a catalyst must be prepared, and so forth when it is first used. Furthermore, the rate at which the oxygen is removed is not consistent, making it difficult to achieve uniform culture conditions.

When "Anaeropack" is used, on the other hand, the carbon dioxide concentration in the culture environment increases, leading to drawbacks in that the influence of the carbon dioxide, which continues to dissolve into the culture medium, lowers the culture pH and affects cell culture.

SUMMARY OF THE INVENTION

An object of the present invention is to remedy the aforementioned drawbacks of the conventional technology. That is, the invention is intended to provide an easily handled gas concentration adjusting agent which allows a low oxygen concentration environment, such as an ischemic environment for tests of cultured cell damage caused by low oxygen or the like, to be conveniently created, as well as a method and a system for adjusting gas concentrations using this easily handled agent.

As a result of extensive, painstaking research undertaken in view of the drawbacks in the conventional technology, the inventors perfected the present invention upon discovering that a low oxygen concentration environment serving as an ideal model test system of ischemic states could be readily obtained by using a gas concentration adjusting agent obtained by combining a carbon dioxide gas absorbent and an ascorbic acid-based oxygen absorbent capable of absorbing oxygen as well as producing carbon dioxide gas, so as to adjust the atmosphere inside a sealed receptacle to an oxygen concentration of no more than 1% and a carbon dioxide concentration of between 3 and 7%.

Specifically, the present invention is intended to provide a gas concentration adjusting agent comprising a composition containing an ascorbic acid, a metal salt, a porous carrier, an alkaline earth metal hydroxide, and water, wherein said composition is housed inside a sealed receptacle in order to absorb the oxygen inside said receptacle, so as to adjust the oxygen concentration inside said receptacle to no more than 5% within 30 minutes and no more than 1% within 1 hour and to adjust the carbon dioxide concentration to between 3% and 7% no sooner than 15 minutes to no more than 3 hours, thereby creating an ischemic environment for cultured cells inside the receptacle.

Examples of the aforementioned ascorbic acid include ascorbic acid and erysorbic acid, salts thereof, and mixtures of these, and examples of said metal salt include iron or copper salts.

The aforementioned ascorbic acid can also be an ascorbic acid or erysorbic acid sodium salt or potassium salt aqueous solution. The salt concentration of said aqueous solution can be between 40 and 55 wt %.

Ferrous sulfate heptahydrate, for example, is preferred as the metal salt contained in the gas concentration adjusting agent pertaining to the present invention.

Activated carbon is a desirable example of the porous carrier included in the gas concentration adjusting agent pertaining to the present invention.

The present invention is also intended to provide a gas concentration adjusting method, comprising the steps of housing cultured cells and a gas concentration adjusting agent consisting of a composition containing an ascorbic acid, a metal salt, a porous carrier, an alkaline earth metal hydroxide, and water in a sealed system, and allowing said gas concentration adjusting agent to absorb the oxygen inside said sealed system, so as to adjust the oxygen concentration inside said sealed system to no more than 5% within 30 minutes and no more than 1% within 1 hour and to adjust the carbon dioxide concentration to between 3% and 7% no sooner than 15 minutes to no more than 3 hours, thereby creating an ischemic environment for cultured cells inside said sealed system.

The present invention is also intended to provide a gas concentration adjusting system, comprising a sealed receptacle and a gas concentration adjusting agent which consists of a composition containing an ascorbic acid, a metal salt, a porous carrier, an alkaline earth metal hydroxide, and water, and which is housed inside said sealed receptacle in order to absorb the oxygen inside said receptacle, so as to adjust the oxygen concentration inside said receptacle to no more than 5% within 30 minutes and no more than 1% within 1 hour and to adjust the carbon dioxide concentration to between 3% and 7% no sooner than 15 minutes to no more than 3 hours, thereby creating an ischemic environment for the cultured cells inside the receptacle.

The gas concentration adjusting agent pertaining to the present invention and the gas concentration adjusting method and system involving the use of this agent can be employed to adjust the gas atmosphere in tests conducted in an ischemic environment, that is, a low oxygen concentration environment, such as in tests studying the damage to cultured cells due to low oxygen.

Ascorbic acids capable of both absorbing oxygen as well as producing carbon dioxide are effective as a primary agent in the oxygen absorption achieved with the gas concentration adjusting agent pertaining to the present invention. Alkaline earth metal hydroxides are effective as the carbon dioxide absorbent combined therein. A composition consisting of an ascorbic acid, metal salt, porous carrier, alkaline earth metal hydroxide, and water is used as the gas concentration adjusting agent. In the present invention, the gas concentration adjusting agent is used in the form of a packaged element obtained by packaging the aforementioned composition in a gas-permeable packaging material.

The ascorbic acids used in the present invention include ascorbic acid or erysorbic acid or salts thereof, or mixtures of these. The ascorbic acid or erysorbic acid may be used in the form of a sodium or potassium salt. The ascorbic acid serving as a primary agent in the present invention can thus also be used in the form of an ascorbic acid or erysorbic acid sodium salt or potassium salt aqueous solution.

The salt concentration of the aqueous solution of the ascorbic acid serving as a primary agent should range from 40 to 51 wt %. When the concentration of the primary agent is lower than the aforementioned range, the oxygen absorption rate is retarded, whereas a higher concentration makes it difficult to prepare the adjusting agent, so both should be avoided.

The metal salt is used as a catalyst in the oxygen absorption reaction of the primary agent. Iron or copper salts are preferred as the metal salt. Ferrous sulfate heptahydrate is the most preferable for use in view of its solubility. The proportion in which the metal salt is blended in should range from 5 to 15 weight parts per 100 weight parts primary agent. The metal salt is used while dissolved in an aqueous solution of the aforementioned primary agent.

The ascorbic acid is referred to as the primary agent below, and the aqueous solution in which the primary agent and metal salt are dissolved is simply referred to as the primary agent solution.

The porous carrier is impregnated with the primary agent solution as a support for this solution. Examples of porous carriers include powders such as activated carbon, diatomaceous earth, silica gel, zeolites, pumice, and alumina, or well-known carrier materials such as water absorbent paper and water absorbent resins. In the present invention, however, activated carbon is preferred in view of its ample water absorption as well as its ability to promote the oxygen absorption reaction while generating little heat during the reaction. Particulate activated carbon is even more desirable.

The porous carrier is used in an amount ranging from 30 to 100 weight parts per 100 weight parts primary agent solution. The amount of porous carrier that is blended in must be selected from within the above range so that the alkaline earth metal hydroxide powder is wet by the primary agent solution when the porous carrier impregnated with the primary agent solution is mixed with the alkaline earth metal hydroxide powder.

An alkaline earth metal hydroxide that is microsoluble in water is preferred as the carbon dioxide absorbent in the present invention. The use of a magnesium hydroxide or calcium hydroxide powder is especially preferred. The alkaline earth metal hydroxide is blended in a proportion of 1.6 to 2.5 mol, and preferably 1.8 to 2.2 mol, per mol primary agent ascorbic acid. When the alkaline earth metal hydroxide is blended in a lower amount, the concentration of carbon dioxide does not fall to the prescribed level, whereas when too great an amount is blended in, not only is the carbon dioxide concentration too low, but the oxygen absorption rate drops, resulting in the need for greater amounts of the gas concentration adjusting agent, so the aforementioned range should not be exceeded.

The ascorbic acid serving as the primary agent theoretically absorbs 1 mol oxygen per mol and produces 1 mol carbon dioxide. Here, approximately 90 to 70% of the amount of carbon dioxide gas produced must be absorbed in order to absorb the oxygen in the air inside the receptacle so as to keep the oxygen concentration to no more than 1% and the carbon dioxide concentration between 3 and 7%. Stoichiometrically, about 0.9 to 0.7 mol carbon dioxide must be absorbed per mol consumed primary agent. Stoichiometrically, ¾ mol carbon dioxide gas is absorbed per mol alkaline earth metal hydroxide. As a result, it is calculated that 1.2 to 0.9 mol alkaline earth metal hydroxide is needed per mol consumed primary agent in order to keep the carbon dioxide concentration between 3 and 7%. Although, stoichiometrically, the amount of alkaline earth metal hydroxide thus needed is, for the most part, no more than 1.2 mol per mol consumed primary agent, a greater amount of the alkaline earth metal hydroxide is actually needed. The blending ratio must be selected within the aforementioned range in consideration of the amount of gas concentration adjusting agent that is used, the oxygen absorption rate, and the like.

The method for manufacturing the gas concentration adjusting agent is not particularly limited. The gas concentration adjusting agent is a composition obtained by mixing the aforementioned components. A method that may be adopted, for example, is to mix the aqueous solution primary agent solution) of the primary agent ascorbic acid and the metal salt with the powder carrier to impregnate the carrier, and to then mix in the powder alkaline earth metal hydroxide so that it is dispersed as a coating on the surface.

The gas concentration adjusting agent pertaining to the present invention is used in the form of a packaged element, in which the aforementioned composition is packaged in a gas-permeable packaging material. For convenient use, the gas concentration adjusting agent capable of absorbing oxygen and of producing carbon dioxide should be provided in the form of a single packaged element. However, the gas concentration adjusting agent pertaining to the present invention can also be provided in the form of separately packaged carbon dioxide-producing oxygen absorbent and carbon dioxide absorbent compositions.

The gas-permeable packaging material for the gas concentration adjusting agent should be oxygen- and carbon dioxide-permeable. A packaging material with an oxygen permeability of at least 300 mL/Hr.m$^2$ and a carbon dioxide permeability of at least 300 mL/Hr.m$^2$ is preferred. Well-known gas-permeable packaging materials can be used as the gas-permeable packaging material. Examples include nonwoven fabrics consisting of synthetic fibers, synthetic paper, microporous films, and paper, as well as composite packaging materials in which porous polyethylene, split cloth, or the like has been laminated as a reinforcer.

The gas concentration adjusting agent thus manufactured is stored in a bag or container with low gas permeability, from which it is taken out when used.

The gas concentration adjusting agent must be at least sufficient to absorb the oxygen in the air sealed in the aforementioned receptacle. Stoichiometrically, the amount of oxygen absorbed by the primary agent ascorbic acid is 1 mol oxygen per mol primary agent. The amount of gas concentration adjusting agent used is preferably at least 1.5 times, and even more preferably between 1.8 and 2.5 times, the aforementioned necessary stoichiometric amount, and is determined upon consideration of the oxygen absorption rate or the gas permeability of the aforementioned receptacle.

The sealed receptacle used in the present invention should consist of a material with a low gas permeability and should allow the gas-tightness to be essentially maintained when sealed. The gas-tightness of the receptacle should be such that the amount of external gas penetration is no more than 3%, and preferably no more than 2%, of the volume of the receptacle per day.

The aforementioned sealed receptacle should be large enough to house at least a culture plate and the adjusting agent. The shape of the receptacle is not particularly limited. In general, plastic Petri dishes 35 mm in diameter are frequently used to culture cells. As such, a receptacle large enough to combine several dishes must be selected, and the amount of gas concentration adjusting agent that is used must be determined according to the space volume produced inside.

Conventional pressure-tight containers can be used as the aforementioned receptacle, but plastic containers, bags, and the like having a low gas permeability can also be used. The use of a plastic container with a structure that is easy to seal, in which the container main body and lid are tightened with a seal member fastener, for example, is preferred because it is light-weight and easy to handle. Polyvinylidene chloride-coated plastic film bags and the like can also be used as easily sealed receptacles by simply heat sealing the bag opening, sealing it with a clip, or the like.

DESCRIPTION OF THE PREFERRED EMBODIMENTS

The invention is described with reference to preferred embodiments below.

Preferred Embodiment 1

49 g of particulate activated carbon was impregnated with a solution obtained by dissolving 7 g of ferrous sulfate heptahydrate in 113 g of 50% sodium ascorbate aqueous solution. 36 g magnesium hydroxide was then added to this, and the materials were mixed to homogeneity to prepare a gas concentration adjusting agent starting material powder. A bag (size: 100 mm×140 mm) made of paper (oxygen diffusion rate: 20,000 mL/m.$^2$Hr) laminated on the inside with porous polyethylene film was then filled with 22.7 g of the starting material powder obtained above, and the bag opening was then heat sealed to prepare a gas concentration adjusting agent.

The gas concentration adjusting agent thus prepared was then sealed with 1.6 L of air in a polyvinylidene chloride-coated nylon film bag (size: 250 mm×350 mm). This sealed bag was then kept in a 37° C. thermostatic tank, and the changes in the oxygen concentration and carbon dioxide concentration inside the bag were measured over time. This test for the gas concentration adjusting agent was done three times. The results are given in Table 1.

TABLE 1

| No. | Over time | 30 min. | 1 hour | 1.5 hours | 2 hours | 3 hours |
|---|---|---|---|---|---|---|
| 1 | $O_2$ % | 3.0 | 0.5 | 0.1 | <0.1 | <0.1 |
|   | $CO_2$ % | 6.6 | 6.0 | 4.7 | 4.4 | 3.8 |
| 2 | $O_2$ % | 3.2 | 0.4 | <0.1 | <0.1 | <0.1 |
|   | $CO_2$ % | 6.5 | 6.5 | 5.3 | 4.6 | 3.9 |
| 3 | $O_2$ % | 2.7 | 0.5 | <0.1 | <0.1 | <0.1 |
|   | $CO_2$ % | 6.8 | 6.5 | 5.2 | 4.5 | 3.8 |

Comparative Embodiment 1

49 g of particulate activated carbon was impregnated with a solution obtained by dissolving 6.5 g of ferrous sulfate heptahydrate in 105 g of 50% sodium ascorbate aqueous solution. 20 g magnesium hydroxide was then added to this, and the materials were mixed to homogeneity to prepare a gas concentration adjusting agent starting material powder. A bag made of paper and porous polyethylene film was then filled with 20 g of the starting material powder obtained above in the same manner as in Preferred Embodiment 1 to prepare a gas concentration adjusting agent.

The gas concentration adjusting agent thus prepared was then sealed with 1.6 L of air in a nylon film bag in the same manner as in Preferred Embodiment 1, and this sealed bag was then kept in a 37° C. thermostatic tank to measure the changes in the oxygen concentration and carbon dioxide concentration inside the bag over time. The results are given in Table 2.

TABLE 2

| No. | Over time | 30 min. | 1 hour | 1.5 hours | 2 hours | 3 hours |
|---|---|---|---|---|---|---|
| 1 | $O_2$ % | 0.5 | <0.1 | <0.1 | <0.1 | <0.1 |
|   | $CO_2$ % | 10.9 | 10.4 | 9.9 | 9.6 | 8.4 |
| 2 | $O_2$ % | 0.4 | <0.1 | <0.1 | <0.1 | <0.1 |
|   | $CO_2$ % | 11.4 | 10.5 | 10.0 | 9.7 | 9.1 |
| 3 | $O_2$ % | 0.2 | <0.1 | <0.1 | <0.1 | <0.1 |
|   | $CO_2$ % | 10.7 | 9.6 | 9.0 | 8.7 | 8.0 |

Preferred Embodiment 2

Figure 4:
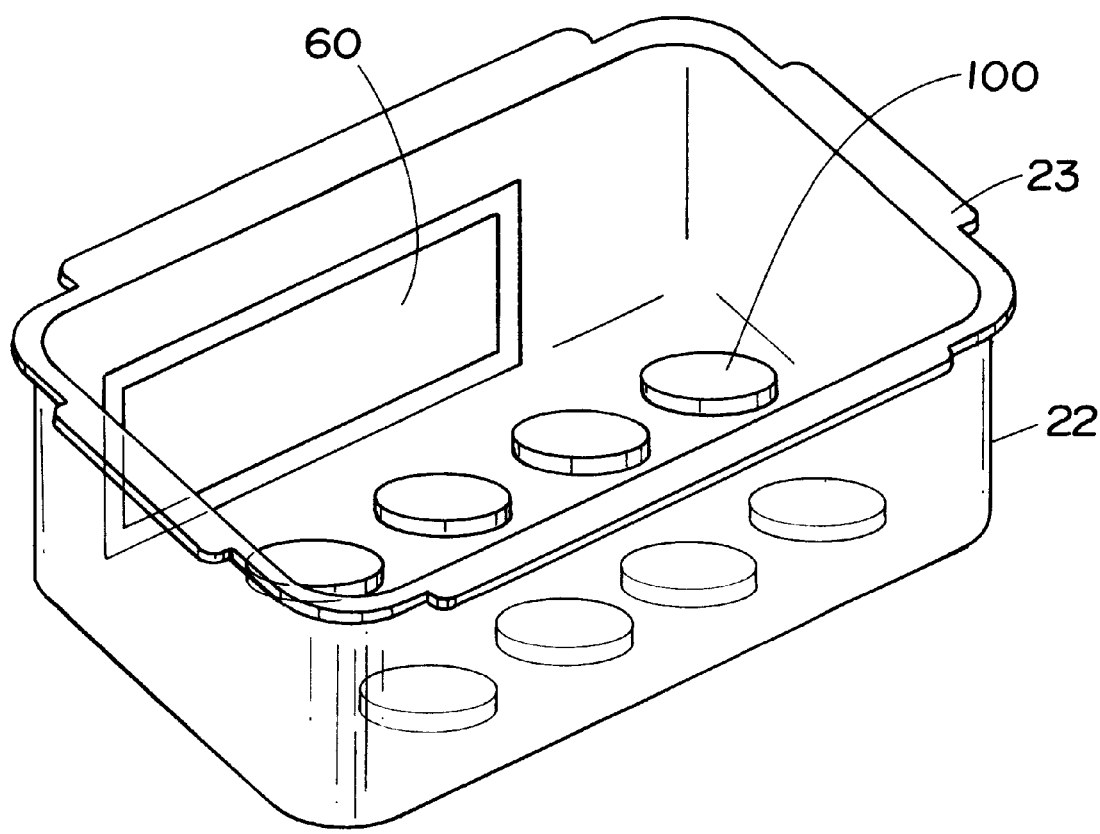
FIG. 4 is an oblique view depicting the gas concentration adjusting agent in a preferred embodiment of the present invention.

The gas concentration adjusting agent prepared in Preferred Embodiment 1 was sealed in a rectangular parallelepiped jar (internal volume of 1.6 L) made by Mitsubishi Petrochemical, as shown in FIG. 4, along with 35 mm diameter plastic Petri dishes filled with 2.0 mL Williams Medium E culture medium (by Gibco BRL).

Specifically, the rectangular parallelepiped jar was equipped with a clear plastic cornered lid (not shown in figure) and a main body 22 covered by this lid, with the lid and main body 22 having a plate-shaped edge 23 mutually joined on four sides. A sealing material was inserted between the plate-shaped edges 23, and the lid and main body 22 were tightened with a fastener, so that the lid and main body 22 were pressure bonded via the seal. As a result, the sealed space formed by the lid and main body 22 was sealed off from the environment outside the rectangular parallelepiped jar.

In this preferred embodiment, a gas concentration adjusting agent 60 and the aforementioned Petri dishes 100 were sealed inside the rectangular parallelepiped jar, and the rectangular parallelepiped jar was kept in a 37° C. thermostatic tank to check the changes in pH over time. The results are given in Table 3.

Comparative Embodiment 2

The gas concentration adjusting agent prepared in Preferred Embodiment 1 was sealed in a rectangular parallelepiped jar (internal volume of 1.6 L) made by Mitsubishi Petrochemical, in the same manner as in Preferred Embodiment 2, along with 35 mm diameter plastic Petri dishes filled with 2.0 mL Williams Medium E culture medium (by Gibco BRL). The jar was then kept in a 37° C. thermostatic tank to check the changes in the pH of the culture medium over time. The results are given in Table 3.

TABLE 3

| | After 0 hour | After 1 hour | After 2 hours | After 3 hours |
|---|---|---|---|---|
| Preferred Embodiment 2 | 7.4 | 7.4 | 7.4 | 7.4 |
| Comparative Embodiment 2 | 7.4 | 7.2 | 7.2 | 7.2 |

At 7.4, the culture medium pH was maintained at the original culture medium pH, as shown in Table 3, in the case of Preferred Embodiment 2, which involved the use of the gas concentration adjusting agent of Preferred Embodiment 1. This demonstrated that the gas concentration adjusting agent of Preferred Embodiment 1, which did not result in a drop in the culture medium pH, was desirable as an agent for adjusting the culture environment under ischemic conditions.

In contrast, in Comparative Embodiment 2 involving the use of the gas concentration adjusting agent of Comparative Embodiment 1, the culture medium pH dropped to 7.2. This pH of 7.2 generally corresponds to the symptoms of acidosis in the human body.

Preferred Embodiment 3

The livers of male Wister rats were perfused with a calcium chelating agent and collagenase, followed by mechanical dispersion with the use of a measuring cylinder and pipet in balanced saline. The hepatic cells alone were collected by centrifugation from this suspension. The hepatic cells were then cultured in 1.5 mL Williams Medium E in 35 mm diameter plastic Petri dishes to prepare first generation cultured hepatic cells.

A low oxygen injury test was conducted as follows using the first generation hepatic cells which had thus been manufactured.

Plastic dishes in which the first generation hepatic cells had been cultured and the gas concentration adjusting agent prepared in Preferred Embodiment 1 were introduced into the aforementioned rectangular parallelepiped jar (1.6 L, by Mitsubishi Petrochemical) and sealed. The sealed jar was then kept for a prescribed period of time in a 37° C. thermostatic tank, the jar lid was then opened, and the jar was allowed to stand while open. The test was conducted by changing the times for which the jars were kept sealed to 2, 3, and 4 hours.

While the jars were sealed in this test, the first generation cultured hepatic cells in the jars were in a low oxygen state reflecting the ischemic conditions of biological livers. Opening the jar lids resulted in a reoxygenated state reflecting the recirculation of blood in biological livers.

In this preferred embodiment, several rectangular parallelepiped jars were prepared, and the low oxygen injury test was conducted with low oxygen states lasting 2, 3, and 4 hours in several test groups.

The test groups were used to measure the following over time:

(1) lactic acid dehydrogenase activity (LDH) leaking in the culture broth as an index of cell membrane damage;

(2) ketone body ratio (KBR: acetoacetic acid/b-hydroxybutyric acid ratio) in culture broth, which is proportional to the $NAD^+/NADH$ ratio as an index of oxidative phosphorylation involved in enzyme absorption by hepatic mitochondria; and (3) concentration (acetoacetic acid+b-hydroxybutyric acid) of ketone bodies produced in culture broth as an index of enzyme function in hepatic mitochondria. The length of the low oxygen times and the changes in these indices in low oxygen and reoxygenated states were compared. Tests with no low oxygen states were similarly carried out on control groups. The measured results for these indices are given in FIGS. 1, 2, and 3.

Test Results of (1)

Figure 1:
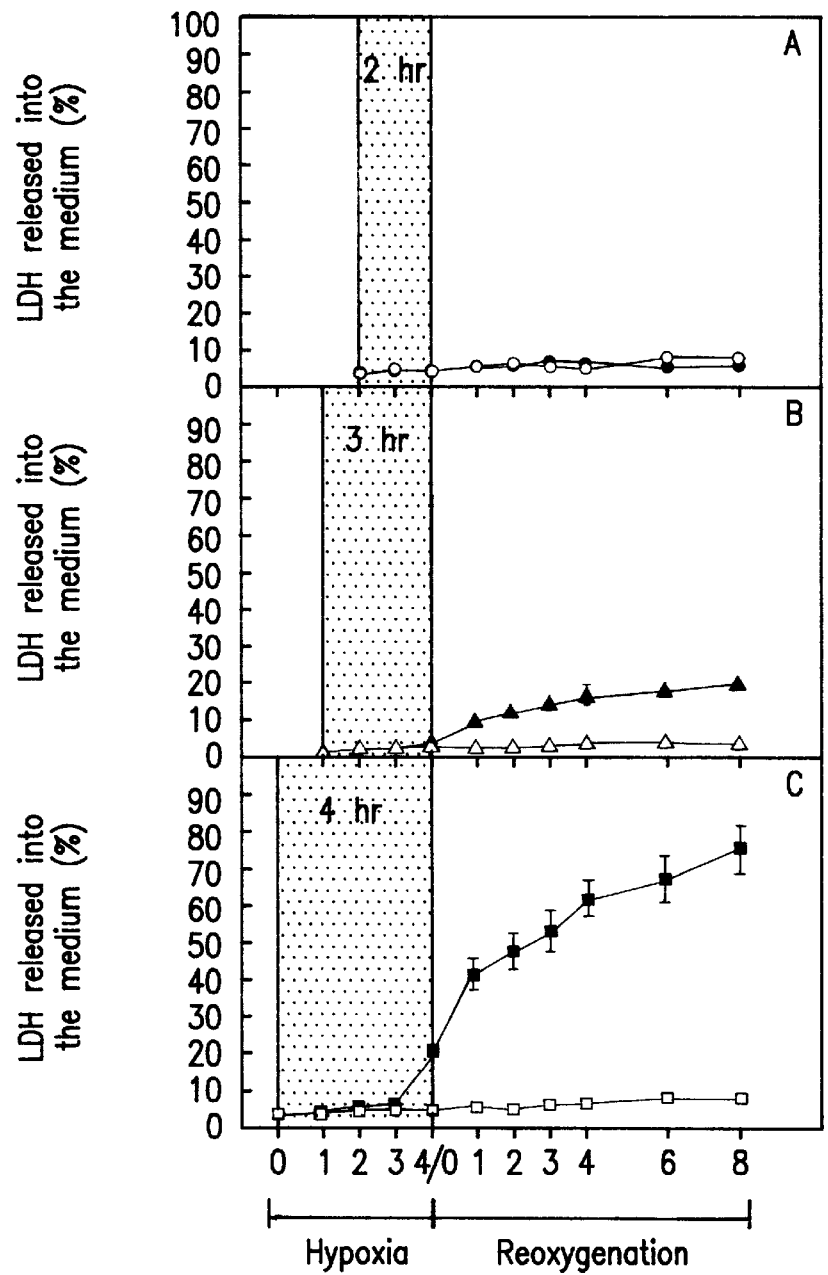
FIG. 1 depicts changes in the leakage of LDH (lactic acid dehydrogenase activity) in culture media under low oxygen conditions and reoxygenated conditions.

As shown in FIG. 1, which depicts the changes over time in the amount of LDH leaking in the culture broth, there was no LDH leakage during low oxygen and reoxygenation states in the 2 hour low oxygen injury test. Although no LDH leakage was observed in the low oxygen state in the 3 hours low oxygen injury test, a slight increase in LDH was noted after reoxygenation, suggesting that hepatic cell injury had occurred. In the 4 hour low oxygen injury test, there was an increase in LDH in the 4th hour following the beginning of low oxygen conditions, with a further increase after reoxygenation.

Test Results of (2)

Figure 2:
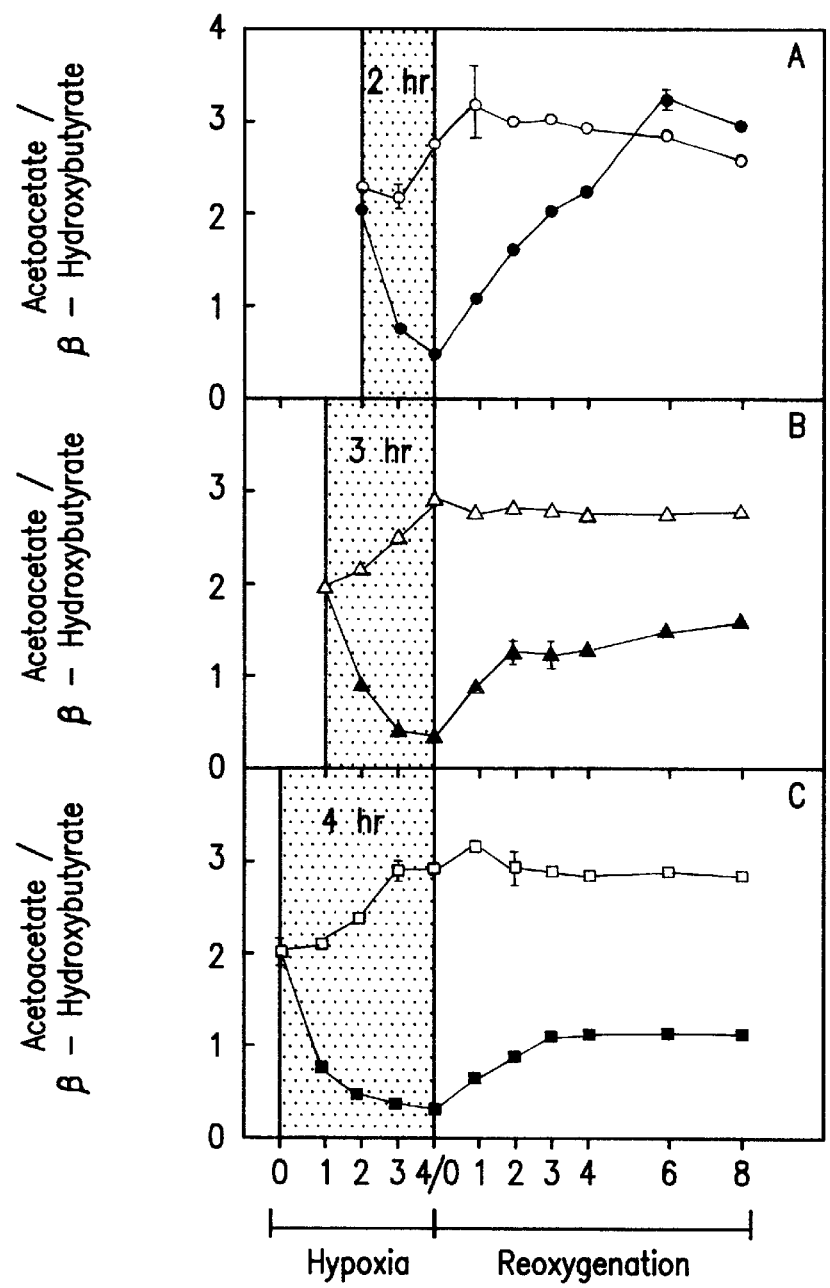
FIG. 2 depicts changes in KBR (ketone body ratio) under low oxygen conditions and reoxygenation conditions.

As shown in FIG. 2, which depicts the changes over time in KBR, there was a marked decrease in all groups in the low oxygen state, but the KBR rapidly returned to previous values after reoxygenation in the 2 hour low oxygen injury test, whereas the recovery of the KBR after reoxygenation was limited in the 3 hour low oxygen injury test, with virtually no recovery of the KBR in the 4 hour group, demonstrating that phosphorylation was adversely affected.

Test Results of (3)

Figure 3:
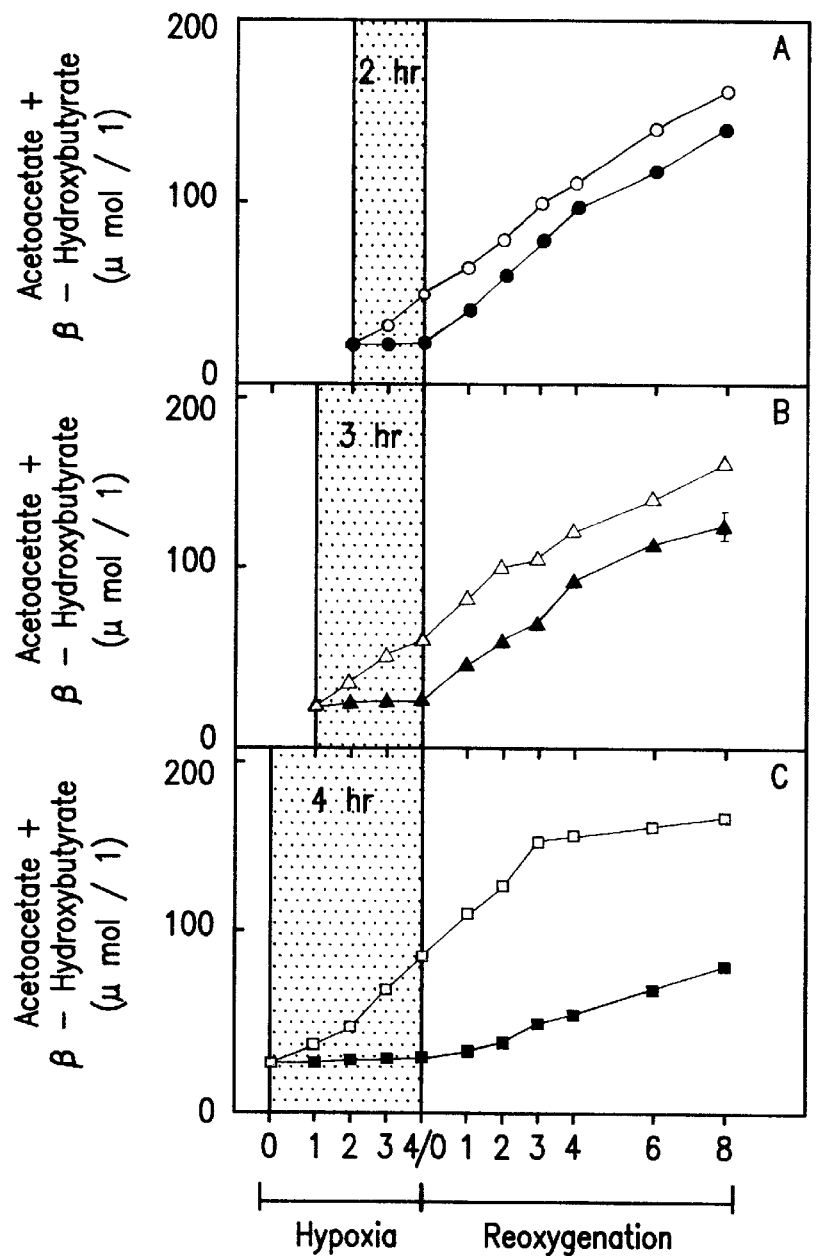
FIG. 3 depicts the course of ketone body production in culture broth under low oxygen conditions and reoxygenation conditions.

As shown in FIG. 3, the production of ketone bodies in the culture broth was virtually completely stopped in all groups in a low oxygen state. Production did recommence after reoxygenation, but the amounts produced were suppressed the longer the low oxygen period, thus revealing that the enzyme function of hepatic mitochondria was impaired depending on the length of the low oxygen state.

The low oxygen and reoxygenation states in the low oxygen injury tests of first generation cultured hepatic cells conducted in this preferred embodiment well reflected the function and morphology of the hepatitic cell states prevailing in the ischemic and blood recirculation states of biological livers, making low oxygen injury tests using the agent for adjusting culture environments in the present invention extremely useful as a model test system for research on damage occurring as a result of warm blood flow impairment and recirculation.

The gas concentration adjusting agent and gas concentration adjusting method in the present invention thus characteristically allow the gas environment inside a sealed container to be made into an environment suitable for low oxygen injury tests of cultured cells, and have led to the development of a way to regulate culture environments using a light weight, easily sealed container and an easily handled gas concentration adjusting agent.

That is, the present invention allows low oxygen injury tests of cells to be carried out by introducing a sealed container containing a gas concentration adjusting agent and culture medium inoculated with cells in a common laboratory chick incubator, thermostatic culture vessel, or the like, without any need for expensive, large-scale equipment, when producing an environment for low oxygen injury tests of cultured cells.

Several systems can be started simultaneously, allowing research efficiency to be improved and operating time to be shortened. As a result, low oxygen injury tests of cultured cells and research on low oxygen and ischemic states can be carried out conveniently, inexpensively, and efficiently at numerous medical research facilities.

The test materials in the present invention are not necessarily limited to cultured cells. Any test material may be used as long as the objectives can be reached using the method of the present invention, allowing the present invention to be widely adapted as a deoxygenation method.

What is claimed is:

1. A gas concentration adjusting system for creating an ischemic environment, comprising:

a sealed receptacle; and a gas concentration adjusting agent comprising a composition containing an organic acid selected from the group consisting of ascorbic acid, erysorbic acid, salts thereof, and mixtures thereof; a metal salt catalyst; a porous carrier; an alkaline earth metal hydroxide to absorb $CO_2$; and water; said agent being housed inside said sealed receptacle in order to absorb the oxygen inside said receptacle, so as to adjust the oxygen concentration inside said receptacle to no more than 5% by volume within 30 minutes and no more than 1% by volume within 1 hour and to adjust the carbon dioxide concentration to between 3% and 7% by volume no sooner than 15 minutes to no more than 3 hours.

2. A gas concentration adjusting system according to claim 1, wherein said metal salt catalyst comprises at least one of iron salt and copper salt.

3. A gas concentration adjusting system according to claim 1, wherein cultured cells are placed in the receptacle in said ischemic environment.

4. A gas concentration adjusting system according to claim 1, wherein said organic acid is present as a sodium and/or potassium salt in an aqueous solution.

5. A gas concentration adjusting system according to claim 4, wherein the salt concentration of said aqueous solution is between 40 and 55 wt %.

6. A gas concentration adjusting system according to claim 1, wherein said metal salt and said alkaline earth metal hydroxide comprising said gas concentration adjusting agent is respectively between 5 and 15 weight parts per 100 weight parts of said organic acid, and between 1.6 and 2.5 mol per said mol of said organic acid.

7. A gas concentration adjusting system according to claim 6, wherein said alkaline earth metal hydroxide is between 1.8 and 2.2 mol per said mol of organic acid.

* * * * *